(12) United States Patent
Ueda et al.

(10) Patent No.: US 11,800,654 B2
(45) Date of Patent: Oct. 24, 2023

(54) DEVICE HAVING CIRCUIT MEMBERS BETWEEN OVERLAPPING SEALING MEMBERS

(71) Applicant: Japan Aviation Electronics Industry, Limited, Tokyo (JP)

(72) Inventors: Shinji Ueda, Tokyo (JP); Seiya Takahashi, Tokyo (JP); Hiroshi Akimoto, Tokyo (JP)

(73) Assignee: Japan Aviation Electronics Industry, Limited, Tokyo (JP)

( * ) Notice: Subject to any disclaimer, the term of this patent is extended or adjusted under 35 U.S.C. 154(b) by 0 days.

(21) Appl. No.: 17/700,748

(22) Filed: Mar. 22, 2022

(65) Prior Publication Data

US 2022/0322518 A1 Oct. 6, 2022

(30) Foreign Application Priority Data

Apr. 5, 2021 (JP) .................. 2021-064377

(51) Int. Cl.
*H05K 5/00* (2006.01)
*H05K 1/02* (2006.01)
(52) U.S. Cl.
CPC ......... *H05K 5/0069* (2013.01); *H05K 1/0298* (2013.01); *H05K 2201/09109* (2013.01)
(58) Field of Classification Search
CPC ............. H01M 50/105; H01M 50/136; H05K 9/0043; H05K 5/0095; H05K 5/069; H05K 5/068
See application file for complete search history.

(56) References Cited

U.S. PATENT DOCUMENTS 5,000,256 A 3/1991 Tousignant
5,285,619 A * 2/1994 Jones ............... H05K 9/0043
53/472

(Continued)

FOREIGN PATENT DOCUMENTS

JP H08-235935 A 9/1996
JP H11-126037 A 5/1999

(Continued)

OTHER PUBLICATIONS

Extended European Search Report in EP 22165011.2-1212, dated Sep. 26, 2022.

(Continued)

*Primary Examiner* — James Wu
(74) *Attorney, Agent, or Firm* — Collard & Roe, P.C.

(57) ABSTRACT

A device includes a first sealing member, a second sealing member, a first circuit member and a second circuit member. The first sealing member basically includes a first film formed with an opening and includes a frame film. At least one of the first circuit member and the second circuit member includes an exposed portion and a seal portion which surrounds the exposed portion. The frame film has a film-seal portion and a circuit-seal portion. The film-seal portion is bonded to the first film to surround the opening. The circuit-seal portion is bonded to the seal portion to surround the exposes portion. The device is formed with a closed space which is enclosed by the first sealing member and the second sealing member. The exposed portion is exposed to the outer space located outside the device.

5 Claims, 8 Drawing Sheets

(56) References Cited

U.S. PATENT DOCUMENTS

| | | | |
|---|---|---|---|
| 5,403,973 A * | 4/1995 | Santilli | H05K 3/284 |
| | | | 174/15.1 |
| 5,406,945 A | 4/1995 | Riazzi et al. | |
| 5,689,878 A * | 11/1997 | Dahringer | H05K 3/284 |
| | | | 29/841 |
| 8,044,415 B2 | 10/2011 | Messere et al. | |
| 9,770,182 B2 | 9/2017 | Bly et al. | |
| 2009/0022949 A1 | 1/2009 | Horita et al. | |
| 2009/0076363 A1 | 3/2009 | Bly et al. | |
| 2019/0287892 A1 | 9/2019 | Saeaeski et al. | |
| 2021/0020528 A1 | 1/2021 | Meier et al. | |
| 2022/0192043 A1 | 6/2022 | Ueda et al. | |
| 2022/0319938 A1 | 10/2022 | Ueda et al. | |

FOREIGN PATENT DOCUMENTS

| | | |
|---|---|---|
| JP | 2000-173394 A | 6/2000 |
| JP | 2001-332654 A | 11/2001 |
| JP | 2004-119559 A | 4/2004 |
| JP | 2004-342967 A | 12/2004 |
| JP | 2006-024054 A | 1/2006 |
| JP | 2007-235045 A | 9/2007 |
| JP | 2009-512977 A | 3/2009 |
| JP | 2015-019020 A | 1/2015 |
| JP | 2018-106796 A | 7/2018 |

OTHER PUBLICATIONS

Extended European Search Report in EP 22165018.7-1212, dated Sep. 27, 2022.

\* cited by examiner

DEVICE HAVING CIRCUIT MEMBERS BETWEEN OVERLAPPING SEALING MEMBERS

CROSS REFERENCE TO RELATED APPLICATIONS

This application is based on and claims priority under 35 U.S.C. § 119 to Japanese Patent Application No. JP 2021-064377 filed Apr. 5, 2021, the content of which is incorporated herein in its entirety by reference.

BACKGROUND OF THE INVENTION

This invention relates to a device comprising a circuit member sealed by a film.

For example, a device which can be made thinner is disclosed in JP2001-332654A (Patent Document 1), the content of which is incorporated herein by reference.

Referring to FIG. 14, Patent Document 1 discloses a module (device) 90 with built-in semiconductor chips. The device 90 comprises a thermosetting resin composition (sealing resin) 92 and a circuit member 94 including semiconductor chips 96 and wiring patterns 98. The sealing resin 92 is formed so that the circuit member 94 is embedded therewithin. Then, a surface of the sealing resin 92 is polished so that the device 90 is made thinner.

Further reduction in thickness is required for a device comprising a circuit member.

SUMMARY OF THE INVENTION

It is therefore an object of the present invention to provide a new device which can be made thinner.

An aspect of the present invention provides a device comprising a first sealing member, a second sealing member, a first circuit member and a second circuit member. The first sealing member comprises, as a base of the first sealing member, a first film formed of a film and comprises a frame film formed of a film. The first film is formed with an opening. The opening is surrounded by an edge portion which forms a closed path. The frame film has a closed path shape. At least one of the first circuit member and the second circuit member comprises an exposed portion and a seal portion. The exposed portion and the seal portion face the first film. The seal portion surrounds the exposed portion throughout its entire circumference. The frame film has a film-seal portion and a circuit-seal portion. The film-seal portion is bonded to the first film so as to surround the opening throughout its entire circumference. The circuit-seal portion is bonded to the seal portion so as to surround the exposes portion throughout its entire circumference. The device is formed with a closed space. The closed space is enclosed by the first sealing member and the second sealing member except for the exposed portion and is shut off from an outer space located outside the device. The exposed portion is exposed to the outer space located outside the device. The first circuit member and the second circuit member except the exposed portion are shut in the closed space. The first circuit member comprises a first contact point. The second circuit member comprises a second contact point. The first contact point and the second contact point are pressed against each other to be in contact with each other in the closed space.

According to the device of an aspect of the present invention, the first sealing member and the second sealing member overlap with each other while the first circuit member and the second circuit member (hereafter, simply referred to as "circuit members") are sandwiched therebetween. The first sealing member is basically formed of a film. Moreover, the structure of each of the circuit members is not restricted except that each of the circuit members should be provided with the contact point. Thus, each of the circuit members of an aspect of the present invention has a simple structure and can be formed of various material. For example, each of the circuit members may be an insulation film formed with a conductive pattern having the contact point. In this instance, the thickness of the entire device can be made extremely thin. Thus, an aspect of the present invention provides a new device which can be made thinner.

An appreciation of the objectives of the present invention and a more complete understanding of its structure may be had by studying the following description of the preferred embodiment and by referring to the accompanying drawings.

Figure 1:
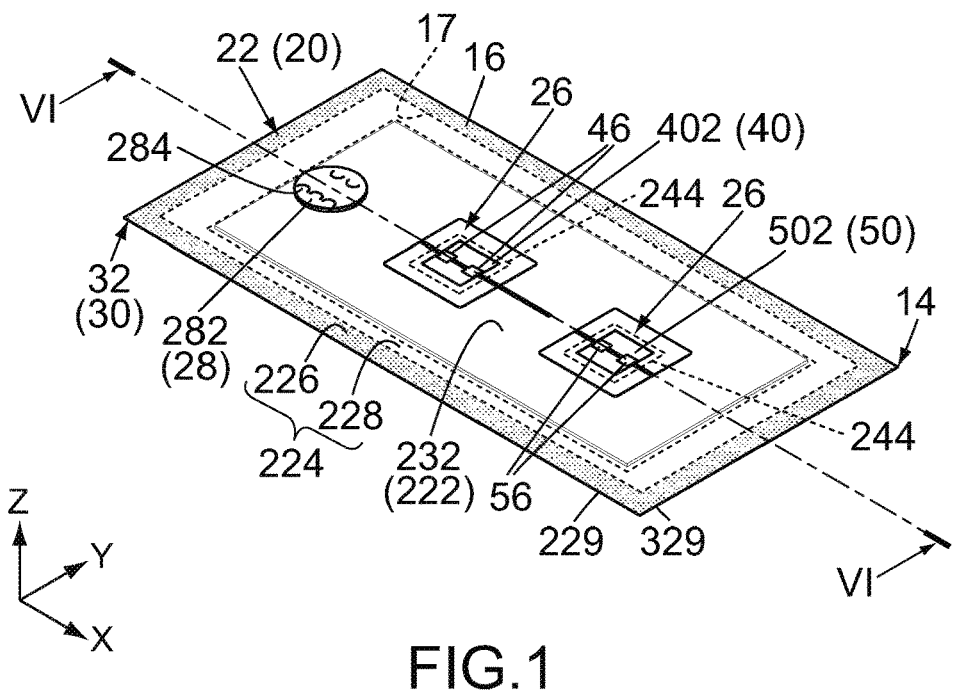
FIG. 1 is a perspective view showing a device according to an embodiment of the present invention, wherein outlines of hidden openings of a first film and boundary lines of a contact region formed between a first sealing member and a second sealing member are illustrated with dashed line.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

Referring to FIG. 1, a device 10 according to an embodiment of the present invention is an independent electronic device. More specifically, the device 10 can work solely without another electronic device (not shown) physically attached thereto. For example, the device 10 measures the heart rate of a subject by attaching the device 10 near the heart of the subject and transmits the measurement result to another electronic device. Thus, the device 10 can be used as an electronic device for measuring biological information such as heart rate. However, the present invention is not limited thereto but is applicable to various devices having various functions.

Figure 2:
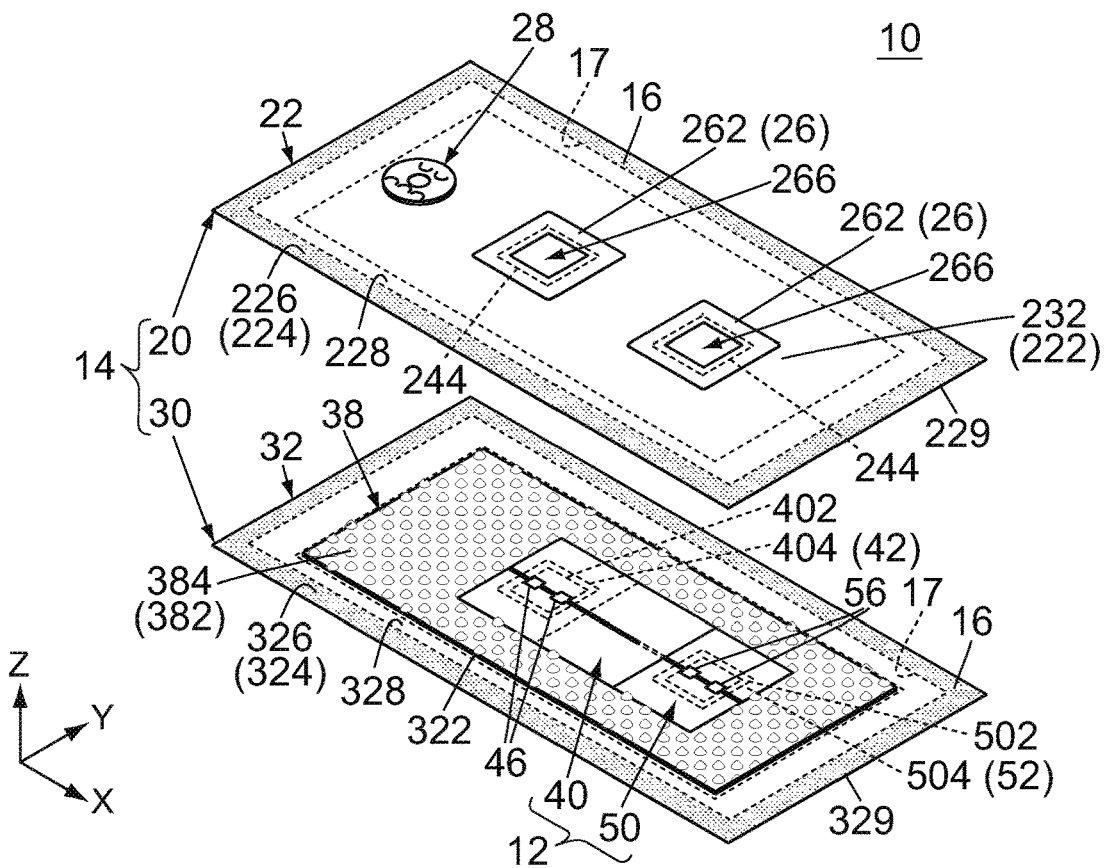
FIG. 2 is a perspective view showing the device of FIG. 1, wherein the first sealing member is removed, and outlines of the hidden openings of the first film, boundary lines of the contact region, position of exposed portions and positions of seal portions are illustrated with dashed line.

Referring to FIG. 2 together with FIG. 1, the device 10 of the present embodiment comprises a circuit structure 12 and a sealing member 14. The circuit structure 12 is a member for enabling the device 10 to work as an electronic device. For example, the circuit structure 12 has an electronic circuit (not shown) for receiving electric signals (hereafter, referred to as "biological signals") generated from electric pulse of the heart of the subject, another electronic circuit (not shown) for measuring the electric pulse of the heart based on the received biological signals and still another electronic circuit (not shown) for transmitting the measurement result to another electronic device (not shown). The sealing member 14 accommodates the circuit structure 12 therewithin and protects the circuit structure 12 from an external environment. Thus, the circuit structure 12 is shut in the sealing member 14.

Figure 9:
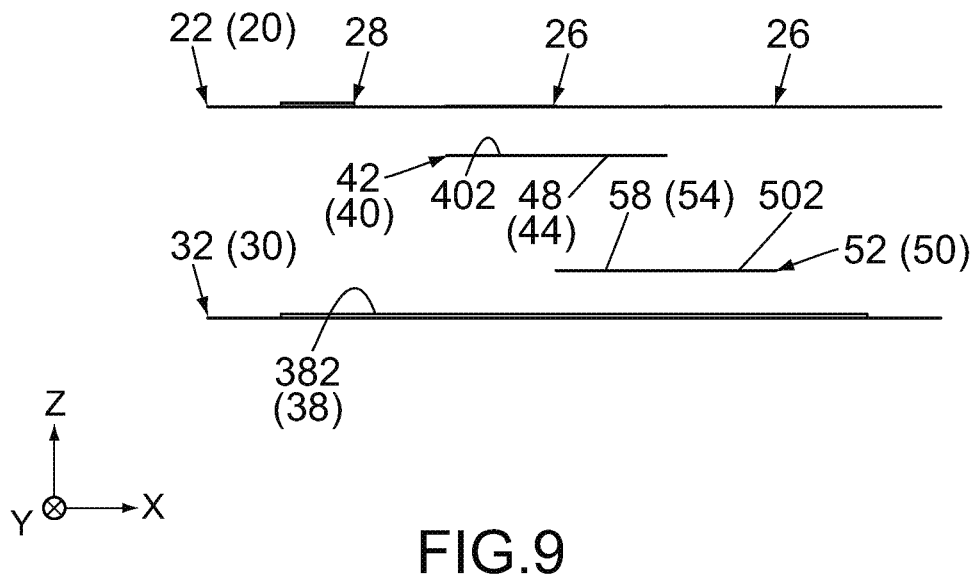
FIG. 9 is a side view showing the device of FIG. 1, wherein the device is under manufacturing process.

The circuit structure 12 of the present embodiment comprises a first circuit member 40 and a second circuit member 50. The sealing member 14 of the present embodiment comprises a first sealing member 20 and a second sealing member 30. Thus, the device 10 comprises the first sealing member 20, the second sealing member 30, the first circuit member 40 and the second circuit member 50. Referring to FIG. 9 together with FIGS. 1 and 2, the four members of the device 10, i.e., the first sealing member 20, the second sealing member 30, the first circuit member 40 and the second circuit member 50, are stacked in an upper-lower direction (Z-direction) and are combined to form the device 10 as a single structure. The device 10 of the present embodiment comprises only the aforementioned four members. However, the present invention is not limited thereto, but the device 10 may further comprise another member in addition to the aforementioned four members.

Hereafter, explanation will be made about each member of the device 10 of the present embodiment.

Figure 6:
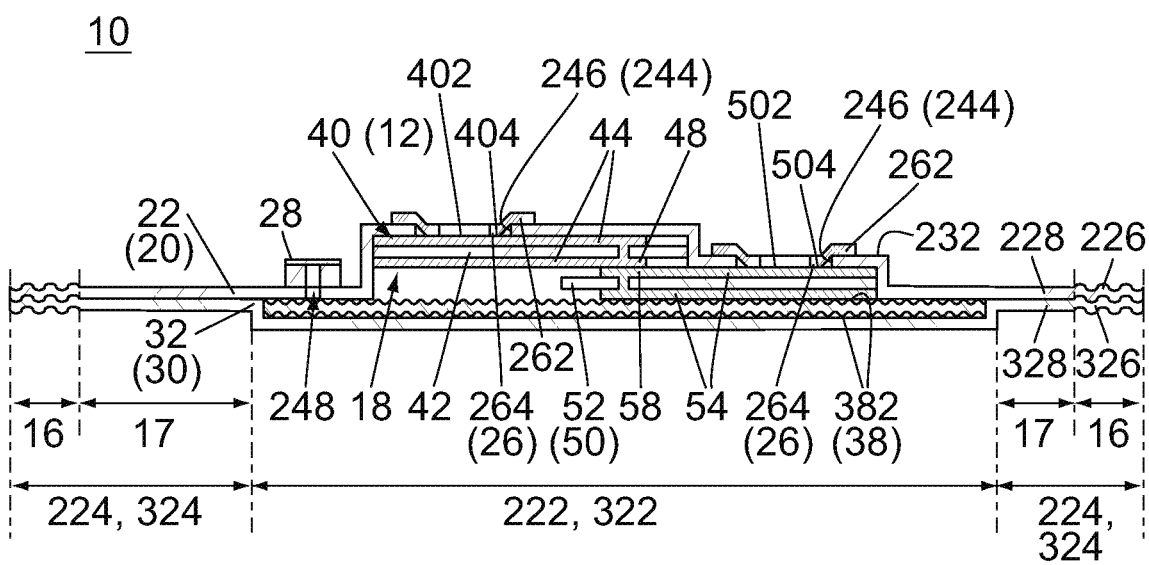
FIG. 6 is a schematic, cross-sectional view showing the device of FIG. 1, taken along line VI-VI, wherein an inner structure of the device is merely schematically illustrated, and the size and arrangement of each member are not equal to the actual size and arrangement thereof.

Referring to FIG. 6, the first sealing member 20 of the present embodiment is formed of, as a base thereof, a first film 22 which is an insulation film. In other words, the first sealing member 20 comprises, as a base of the first sealing member 20, the first film 22 formed of a film. The first film 22 of the present embodiment is a thin, rectangular sheet and is bendable. For example, the first film 22 has a thickness of about 0.01 to 0.5 mm. The first film 22 extends in parallel to a horizontal plane (sheet plane: XY-plane). The first film 22 has a peripheral edge 229 in the XY-plane.

Figure 3:
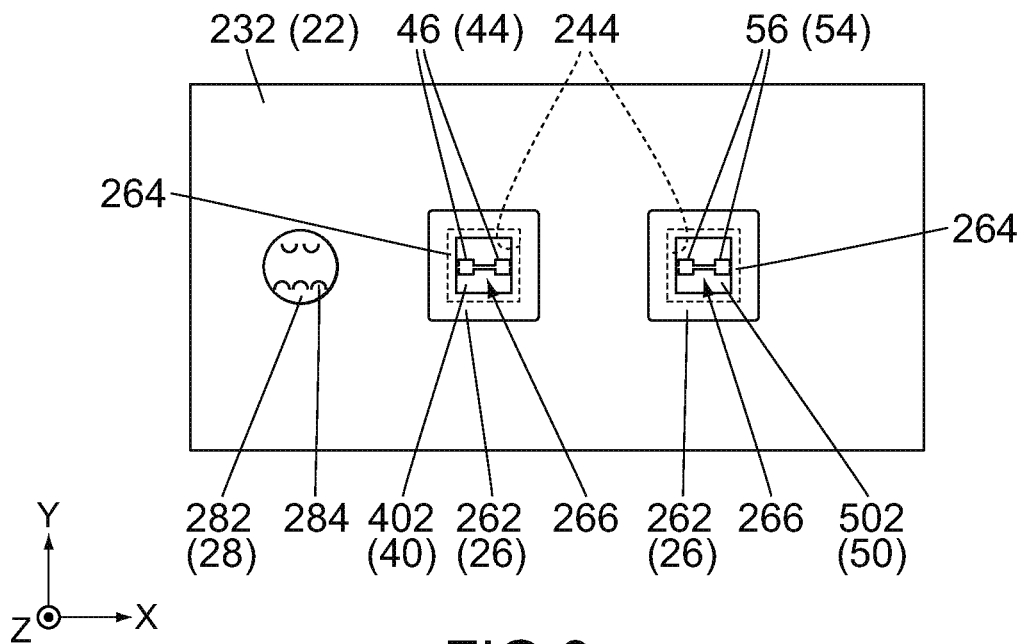
FIG. 3 is a top view showing the device of FIG. 1, wherein outlines of the hidden openings of the first film are illustrated with dashed line.
Figure 4:
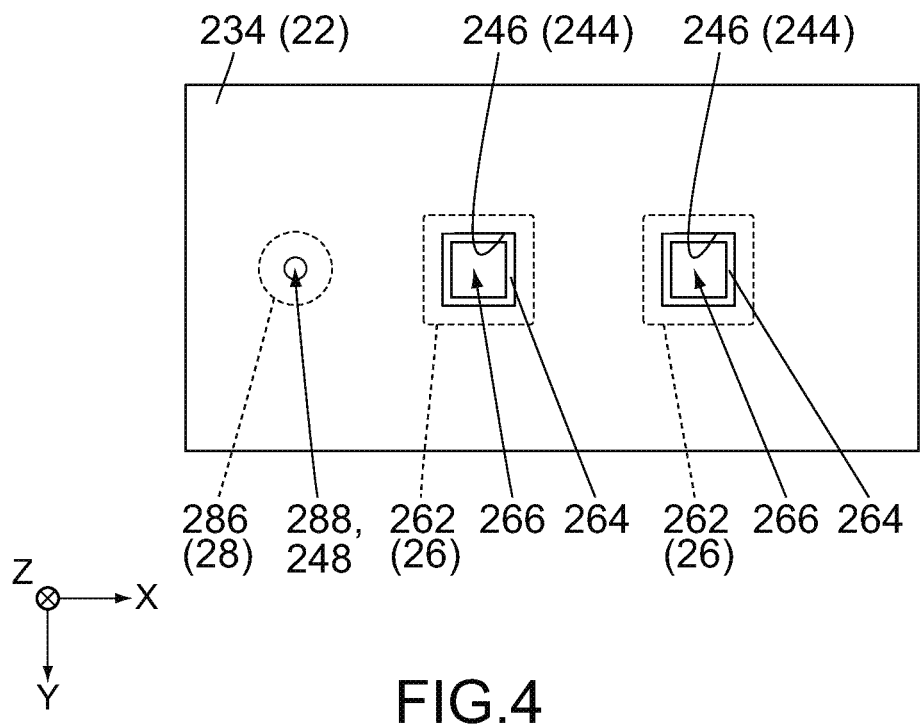
FIG. 4 is a bottom view showing the first sealing member of the device of FIG. 3, wherein hidden outlines of frame films and an air valve are illustrated with dashed line.

Referring to FIGS. 3 and 4, the first film 22 has an outer surface 232 and an inner surface 234. The outer surface 232 is an upper surface (positive Z-side surface) of the first film 22. The inner surface 234 is a lower surface (negative Z-side surface) of the first film 22.

Figure 7:
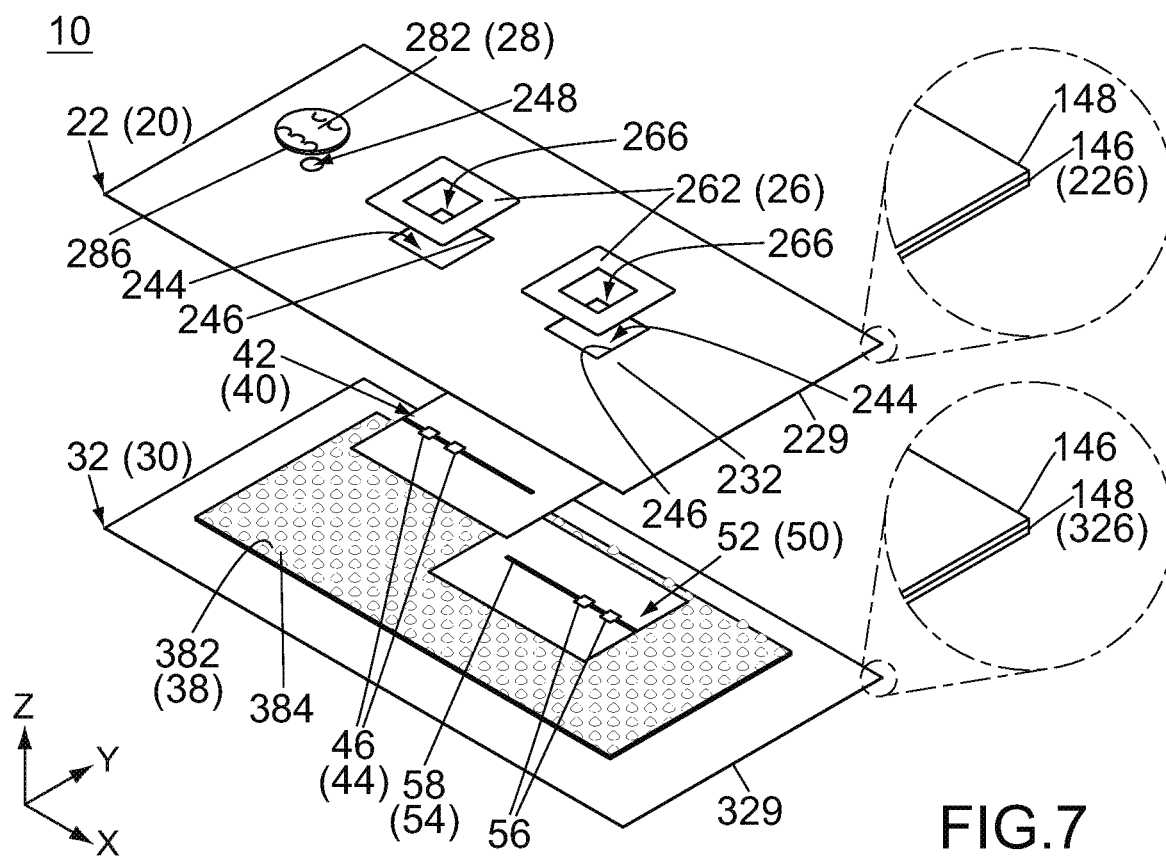
FIG. 7 is an exploded, perspective view showing the device of FIG. 1, wherein a part of the first film enclosed by dashed line and a part of a second film enclosed by dashed line are enlarged and illustrated.

Referring to FIG. 7, the first film 22 of the present embodiment comprises two layers consisting of a meltable layer 146 which is meltable by heat-treatment and an unmeltable layer 148 which is not meltable by heat-treatment. The meltable layer 146 is located under the unmeltable layer 148. For example, the meltable layer 146 is made of polyethylene, and the unmeltable layer 148 is made of nylon. According to this structure, the meltable layer 146 can be fused to another meltable layer of another member while the unmeltable layer 148 is maintained. However, the present invention is not limited thereto. For example, the first film 22 may comprise only one layer which is the unmeltable layer 148 or may comprise three or more layers.

The first film 22 is formed with two openings 244 and a valve opening 248. Each of the openings 244 and the valve opening 248 passes through the first film 22 in the Z-direction. The valve opening 248 has a small circular shape in the XY-plane. The two openings 244 has rectangular shapes which have sizes same as each other in the XY-plane. In detail, each of the openings 244 is formed with an edge portion 246 in the XY-plane. The edge portion 246 of each of the openings 244 forms a closed path. More specifically, each of the edge portions 246 has a seamless frame shape in the XY-plane. However, the present invention is not limited thereto. For example, the shape and the size in the XY-plane of each of the openings 244 and the valve opening 248 are not specifically limited.

Referring to FIGS. 1 and 7, the first sealing member 20 of the present embodiment comprises two frame films 26 each formed of a film and an air valve 28 in addition to the first film 22.

Referring to FIG. 7, each of the frame films 26 has a closed path shape. Each of the frame films 26 of the present embodiment is a thin sheet having a rectangular frame shape and is bendable. Each of the frame films 26 has an outer edge which has a rectangular shape in the XY-plane. Each of the frame films 26 is formed with a center hole 266. Each of the center holes 266 has a rectangular shape in the XY-plane and passes through the frame film 26 in the Z-direction. Each of the frame films 26 of the present embodiment has the aforementioned structure. However, the structure of each of the frame films 26 is not specifically limited, provided that each of the frame films 26 has a closed, or seamless, frame shape. For example, each of the frame films 26 may have a circular frame shape.

Referring to FIGS. 3 and 4, each of the frame films 26 has a film-seal portion 262 and a circuit-seal portion 264. The circuit-seal portion 264 of the present embodiment is a part of the frame film 26 which is located around the center hole 266 and has a rectangular frame shape. The circuit-seal portion 264 surrounds the center hole 266 throughout its entire circumference in the XY-plane. The film-seal portion 262 of the present embodiment is another part of the frame film 26 which is located around the circuit-seal portion 264 and has a rectangular frame shape. The film-seal portion 262 surrounds the circuit-seal portion 264 throughout its entire circumference in the XY-plane. In the present embodiment, there is no visible boundary between the film-seal portion 262 and the circuit-seal portion 264. However, the present invention is not limited thereto. For example, a visible boundary may be formed between the film-seal portion 262 and the circuit-seal portion 264.

Each of the frame films 26 of the present embodiment is formed of an ultraviolet-curing tape. More specifically, each of the frame films 26 contains a pressure-sensitive adhesive which can be adhered to another member when pressed against another member and an ultraviolet-curing resin which can be hardened when exposed to ultraviolet light. Thus, each of the film-seal portions 262 and the circuit-seal portions 264 contains a pressure-sensitive adhesive and an ultraviolet-curing resin. For example, when the film-seal portion 262 is pressed against another member, the frame film 26 is adhered to this member. Thereafter, when ultraviolet light is radiated to the frame film 26, the frame film 26 is hardened to be bonded to this member.

Each of the frame films 26 of the present embodiment has a lower layer (negative Z-side part) and an upper layer (positive Z-side part). The lower layer is made of resin which contains a pressure-sensitive adhesive and an ultraviolet-curing resin. The upper layer is made of resin which contains no pressure-sensitive adhesive and no ultraviolet-curing resin. Thus, each of the film-seal portions 262 and the circuit-seal portions 264 has a lower surface which can be adhered and bonded to another member. In contrast, each of the film-seal portions 262 and the circuit-seal portions 264 has an upper surface which cannot be adhered to another member merely by pressing against another member. However, the present invention is not limited thereto. For example, the resin of the upper layer of the frame film 26 may contain a pressure-sensitive adhesive and an ultraviolet-curing resin similarly to the lower layer.

The two frame films 26 are provided so as to correspond to the two openings 244 of the first film 22, respectively. Each of the openings 244 has a size in the XY-plane which is smaller than a size of the corresponding frame film 26 in the XY-plane but is larger than a size of the center hole 266 of the corresponding frame film 26 in the XY-plane. Each of the frame films 26 is arranged on the outer surface 232 of the first film 22 so that the corresponding opening 244 is located inward of the outer edge of the frame film 26 and is located outward of the center hole 266 in the XY-plane. In other words, each of the frame films 26 is arranged on the outer surface 232 so as to cover the edge portion 246 of the corresponding opening 244 throughout its entire circumference.

The film-seal portion 262 of each of the frame films 26 which are arranged as described above is adhered to the outer surface 232. A part of the film-seal portion 262 which is located around the opening 244 is adhered to the first film 22 throughout entire circumference of the opening 244. The film-seal portion 262 is firmly attached to the outer surface 232 and seals off the edge portion 246 of the opening 244 in the XY-plane throughout its entire circumference. In manufacturing steps of the device 10 described later, the film-seal portion 262 is hardened by radiating ultraviolet light to be bonded to the outer surface 232. Thus, in the fabricated device 10, the film-seal portion 262 is bonded to the first film 22 so as to surround the opening 244 throughout its entire circumference.

The frame film 26 of the present embodiment is boded to the outer surface 232 of the first film 22 by using the pressure-sensitive adhesive and the ultraviolet-curing resin contained in the film-seal portion 262. However, the present invention is not limited thereto. For example, the frame film 26 may be bonded to the outer surface 232 of the first film 22 by using a fixing member other than the frame film 26. When the frame film 26 can be bonded to another member only by using a pressure-sensitive adhesive, the frame film 26 does not need to contain an ultraviolet-curing resin. Thus, the frame film 26 may be a simple adhesive tape.

According to the present embodiment, when the film-seal portion 262 is adhered on the outer surface 232, the circuit-seal portion 264 is located inward of the opening 244 in the XY-plane. In other words, a part of the frame film 26 which is adhered on the outer surface 232 is the film-seal portion 262, and another part of the frame film 26 which is located inward of the opening 244 in the XY-plane so as not to be adhered on the outer surface 232 is the circuit-seal portion 264.

Figure 8:
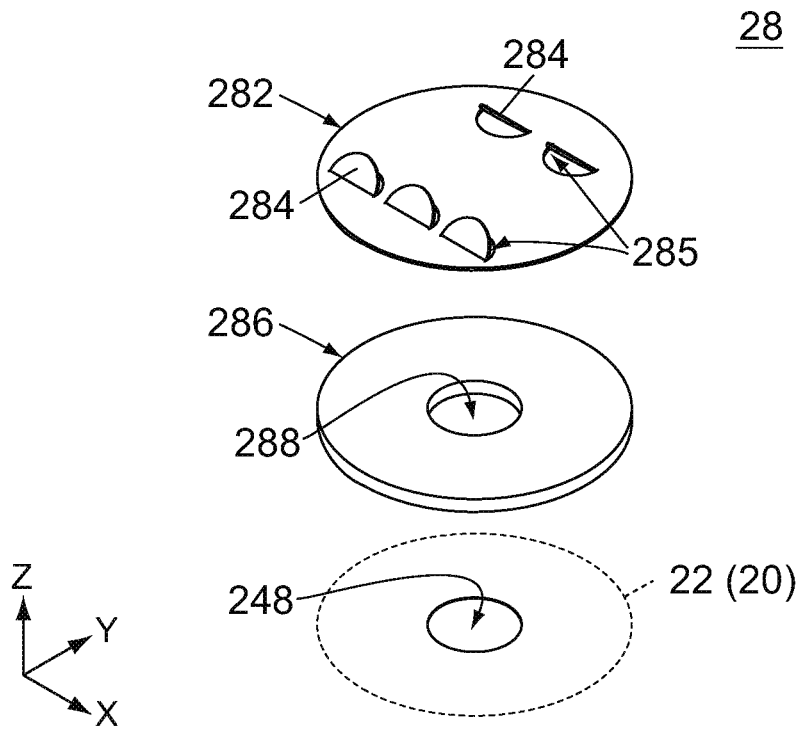
FIG. 8 is a perspective view showing the air valve of FIG. 7, wherein valves of the air valve are open.

Referring to FIGS. 7 and 8, the air valve 28 of the present embodiment comprises a cover portion 282 formed of a thin insulation film and a base portion 286 made of insulator. As shown in FIG. 8, the base portion 286 is formed with a passing hole 288. The passing hole 288 passes through the base portion 286 in the Z-direction. The cover portion 282 is formed with five valves 284 and five cuts 285 which correspond to the valves 284, respectively. Each of the cuts 285 passes through the cover portion 282 in the Z-direction. The valves 284 and the cuts 285 are located inward of an outer circumference of the cover portion 282 in the XY-plane.

Referring to FIG. 8 together with FIG. 7, the cover portion 282 is adhered to and fixed on an upper surface of the base portion 286. In particular, the outer circumference of the cover portion 282 in the XY-plane is tightly adhered to the upper surface of the base portion 286 throughout its entire circumference. In contrast, an inner part of the cover portion 282, which is located inward of the outer circumference of the cover portion 282 in the XY-plane, can be pulled away from the upper surface of the base portion 286. Thus, a passage which allows air to pass therethrough can be formed between the passing hole 288 and each of the cuts 285. The base portion 286 has a lower surface which is adhered to and fixed on the first film 22 in such a way that the passing hole 288 communicates with the valve opening 248 of the first film 22.

Referring to FIG. 1 together with FIG. 8, the air valve 28 can take either an open state shown in FIG. 8 or a closed state shown in FIG. 1. When the air valve 28 takes the open state, each of the valves 284 is apart from the corresponding cut 285. When the air valve 28 takes the closed state, each of the valves 284 completely covers the corresponding cut 285. When the air valve 28 takes the open state, an air passage via the air valve 28 is formed between the inside and the outside of the device 10. When the air valve 28 takes the closed state, the inside of the device 10 is shut off from the outside of the device 10.

As described later, the air valve 28 is used for vacuuming the inside of the device 10 upon fabrication of the device 10. The air valve 28 of the present embodiment has a structure suitable for this use. However, the present invention is not limited thereto. For example, the structure of the air valve 28 is not specifically limited, provided that the inside air of the device 10 can be discharged by using the air valve 28. Moreover, the inside of the device 10 may be vacuumed without provision of the air valve 28. In other words, the first sealing member 20 may comprise the air valve 28 as necessary.

Referring to FIG. 7, the second sealing member 30 of the present embodiment is formed of, as a base thereof, a second film 32 which is an insulation film. In other words, the second sealing member 30 comprises, as a base of the second sealing member 30, the second film 32 formed of a film. The second film 32 of the present embodiment is formed of material similar to that of the first film 22 and has a structure similar to that of the first film 22. For example, the second film 32 is a thin, rectangular sheet and is bendable. The second film 32 extends in parallel to the XY-plane. The second film 32 has a peripheral edge 329 in the XY-plane. However, the present invention is not limited thereto. For example, the second sealing member 30 may comprise, as a base thereof, a rigid circuit board instead of the second film 32. The rigid circuit board may have rigidity and may be hardly bent.

The second film 32 or the rigid circuit board of the present embodiment comprises, similarly to the first film 22, two layers consisting of the meltable layer 146 which is meltable by heat-treatment and the unmeltable layer 148 which is not meltable by heat-treatment. The meltable layer 146 is located over the unmeltable layer 148. According to this structure, the two meltable layers 146 of the first film 22 and the second film 32 can be fused to each other while the unmeltable layers 148 are maintained. However, the present invention is not limited thereto. Each of the first film 22 and the second film 32 may have any structure, provided that it is in accordance with a forming method of the device 10. For example, the first film 22 and the second film 32 may be bonded together by using a fixing member such as an adhesive. In this instance, each of the first film 22 and the second film 32 may comprise only one layer which is the unmeltable layer 148. Instead, each of the first film 22 and the second film 32 may comprise three or more layers.

Referring to FIGS. 2 and 7, the second sealing member 30 of the present embodiment comprises an additional film 38 formed of an insulation film in addition to the second film 32. The additional film 38 has an uneven portion 382. As described later, the uneven portion 382 is provided in order to maintain a passage which allows air to pass therethrough upon vacuuming the inside of the device 10. In detail, the uneven portion 382 is formed with a large number of projections 384. Each of the projections 384 is a projection which projects upward, or in the positive Z-direction, and is resiliently deformable. The projections 384 are uniformly and continuously formed over the entire additional film 38 in the XY-plane. According to the structure described above, a passage which allows air to pass therethrough is formed between every adjacent two of the projections 384. The shape and the size of each of the projections 384 are not specifically limited, provided that the passage which allows air to pass therethrough can be formed.

Referring to FIG. 1 together with FIG. 2, the first film 22 and the second film 32 of the present embodiment overlap with each other so that the position of the peripheral edge 229 and the position of the peripheral edge 329 are aligned with each other in the XY-plane. However, the present invention is not limited thereto. For example, the size of the first film 22 in the XY-plane and the size of the second film 32 in the XY-plane may be different from each other. The shape of each of the first film 22 and the second film 32 is not limited to be rectangular but can be modified as necessary.

Figure 5:
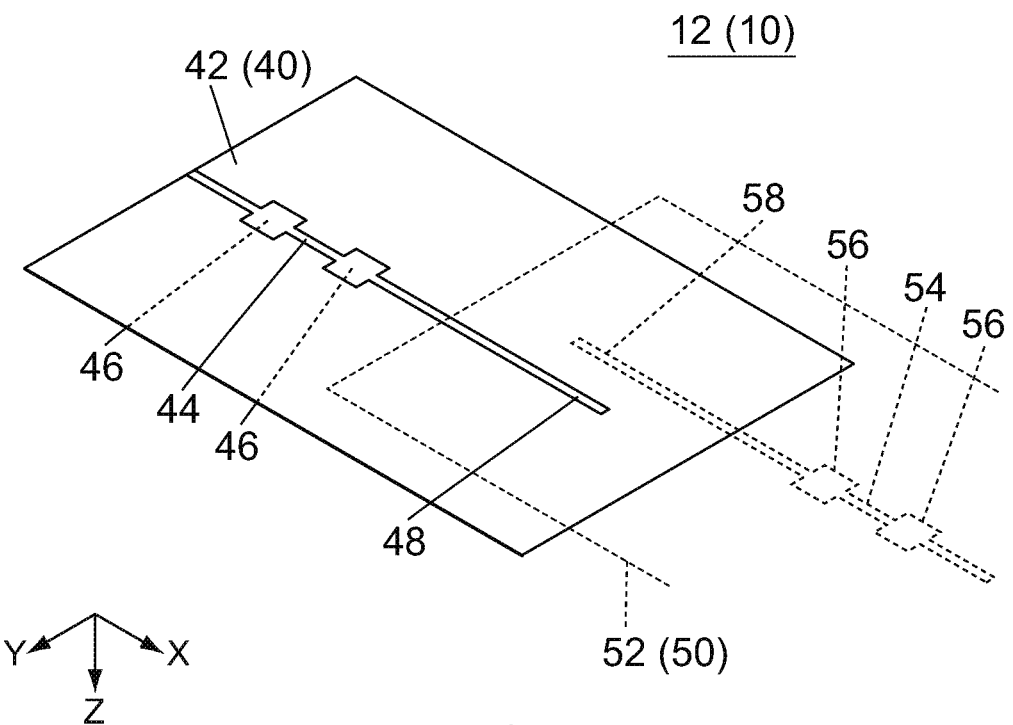
FIG. 5 is a perspective view showing a circuit structure of the device of FIG. 1, wherein a part of a second circuit member is illustrated with dashed line. Although illustrated first and second contact points are apart from each other, the actual first and second contact points are in contact with each other.

Referring to FIGS. 5 and 7, the first circuit member 40 of the present embodiment has a first base portion 42 and a first conductive pattern 44. The first base portion 42 of the present embodiment is a thin, rectangular sheet formed of an insulation film and is bendable. The first base portion 42 extends in parallel to the XY-plane. The first conductive pattern 44 is formed on the first base portion 42. In detail, the first conductive pattern 44 is made of conductor such as copper and is formed on each of upper and lower surfaces of the first base portion 42 by a forming method such as silver ink printing or etching.

Referring to FIG. 6, according to the present embodiment, the first conductive pattern 44 has a first upper conductive pattern 44 which is formed on the upper surface of the first base portion 42 and a first lower conductive pattern 44 which is formed on the lower surface of the first base portion 42. The first upper conductive pattern 44 and the first lower conductive pattern 44 are electrically connected with each other through a via hole formed in the first base portion 42. Referring to FIGS. 5 and 7, the first upper conductive pattern 44 has a structure same as that of the first lower conductive pattern 44 and is located just over the first lower conductive pattern 44. In other words, when the first upper conductive pattern 44 and the first lower conductive pattern 44 are projected on the XY-plane along the Z-direction, the two projected images are completely equal to each other. However, the present invention is not limited thereto. For example, the structure of the first conductive pattern 44 can be modified as necessary.

The second circuit member 50 of the present embodiment has a second base portion 52 and a second conductive pattern 54. The second base portion 52 of the present embodiment is a thin, rectangular sheet formed of an insulation film and is bendable. The second base portion 52 extends in parallel to the XY-plane. The second conductive pattern 54 is formed on the second base portion 52. In detail, the second conductive pattern 54 is made of conductor such as copper and is formed on each of upper and lower surfaces of the second base portion 52 by a forming method such as silver ink printing or etching.

Referring to FIG. 6, according to the present embodiment, the second conductive pattern 54 has a second upper conductive pattern 54 which is formed on the upper surface of the second base portion 52 and a second lower conductive pattern 54 which is formed on the lower surface of the second base portion 52. The second upper conductive pattern 54 and the second lower conductive pattern 54 are electrically connected with each other through a via hole formed in the second base portion 52. Referring to FIGS. 5 and 7, the second upper conductive pattern 54 has a structure same as that of the second lower conductive pattern 54 and is located just over the second lower conductive pattern 54. In other words, when the second upper conductive pattern 54 and the second lower conductive pattern 54 are projected on the XY-plane along the Z-direction, the two projected images are completely equal to each other. However, the present invention is not limited thereto. For example, the structure of the second conductive pattern 54 can be modified as necessary.

Each of the first circuit member 40 and the second circuit member 50 of the present embodiment has the aforementioned structure. However, the present invention is not limited thereto. For example, each of the first circuit member 40 and the second circuit member 50 may be provided with one or more electronic components. One of the first circuit member 40 and the second circuit member 50 may be a single electronic component. Each of the first circuit member 40 and the second circuit member 50 may be a rigid circuit board. The forming method of each of the first conductive pattern 44 and the second conductive pattern 54 is not specifically limited, provided that each of the first conductive pattern 44 and the second conductive pattern 54 is made of conductor.

Referring to FIGS. 5 and 7, the first conductive pattern 44 of the present embodiment has two first terminals 46 and a first contact point 48. The second conductive pattern 54 of the present embodiment has two second terminals 56 and a second contact point 58. Thus, the first circuit member 40 comprises the first terminals 46 and the first contact point 48, and the second circuit member 50 comprises the second terminals 56 and the second contact point 58.

Each of the first terminals 46 is a part of the first upper conductive pattern 44, and the first contact point 48 is a part of the first lower conductive pattern 44. Each of the second terminals 56 and the second contact point 58 is a part of the second upper conductive pattern 54. Thus, the first terminals 46 are located on the upper surface of the first base portion 42, and the first contact point 48 is located on the lower surface of the first base portion 42. The second terminals 56 and the second contact point 58 are located on the upper surface of the second base portion 52.

Referring to FIG. 2, the first circuit member 40 of the present embodiment comprises an exposed portion 402 and a seal portion 404. Each of the exposed portion 402 and the seal portion 404 is a part of an upper surface of the first circuit member 40. The exposed portion 402 and the seal portion 404 face the first film 22 in the Z-direction. The exposed portion 402 of the present embodiment is a rectangular region which includes a part of the upper surface of the first base portion 42 and the two first terminals 46. The seal portion 404 of the present embodiment is a rectangular frame-shaped region which is located around the exposed portion 402 in the XY-plane. The seal portion 404 includes another part of the upper surface of the first base portion 42 and a part of the first conductive pattern 44. The seal portion 404 surrounds the exposed portion 402 throughout its entire circumference in the XY-plane.

The second circuit member 50 of the present embodiment comprises an exposed portion 502 and a seal portion 504. Each of the exposed portion 502 and the seal portion 504 is a part of an upper surface of the second circuit member 50. The exposed portion 502 and the seal portion 504 face the first film 22 in the Z-direction. The exposed portion 502 of the present embodiment is a rectangular region which includes a part of the upper surface of the second base portion 52 and the two second terminals 56. The seal portion 504 of the present embodiment is a rectangular frame-shaped region which is located around the exposed portion 502 in the XY-plane. The seal portion 504 includes another part of the upper surface of the second base portion 52 and a part of the second conductive pattern 54. The seal portion 504 surrounds the exposed portion 502 throughout its entire circumference in the XY-plane.

Referring to FIG. 3, the exposed portion 402 and the exposed portion 502 are provided so as to correspond to the two openings 244, respectively. In the fabricated device 10, each of the exposed portion 402 and the exposed portion 502 is located at the middle of the corresponding opening 244 in the XY-plane. In the fabricated device 10, each of the seal portion 404 and the seal portion 504 is located at an outer circumference of the corresponding opening 244 in the XY-plane and is located just under the circuit-seal portion 264 of the corresponding frame film 26.

In the fabricated device 10, the circuit-seal portions 264 of the two frame films 26 are bonded to the seal portion 404 and the seal portion 504, respectively, by using the pressure-sensitive adhesive and the ultraviolet-curing resin contained in each of the circuit-seal portions 264. However, the present invention is not limited thereto. For example, the circuit-seal portions 264 may be bonded to the seal portion 404 and the seal portion 504, respectively, by using a fixing member such as an adhesive other than the frame film 26.

The circuit-seal portions 264 of the frame films 26 of the present embodiment are bonded to the seal portions 404 and the seal portion 504, respectively, so as to surround the exposed portion 402 and the exposed portion 502 throughout their entire circumferences, respectively. As a result, air passages through the openings 244 are blocked. The shape of each of the exposed portion 402, the exposed portion 502, the seal portion 404 and the seal portion 504 is not specifically limited, provided that the circuit-seal portions 264 can be bonded to the seal portion 404 and the seal portion 504, respectively, so that these air passages are blocked.

In the fabricated device 10, the exposed portion 402 and the exposed portion 502 are exposed upward through the center holes 266 of the frame films 26. In other words, a part of the first circuit member 40 which is exposed through the center hole 266 is the exposed portion 402, and another part of the first circuit member 40 which surrounds the exposed portion 402 in the XY-plane is the seal portion 404. Similarly, a part of the second circuit member 50 which is exposed through the center hole 266 is the exposed portion 502, and another part of the second circuit member 50 which surrounds the exposed portion 502 in the XY-plane is the seal portion 504.

Referring to FIG. 6, the first contact point 48 and the second contact point 58 are in contact with each other in the fabricated device 10. Thus, the first conductive pattern 44 and the second conductive pattern 54 are electrically connected with each other and are electrically connectable with a member located outside the device 10 via the first terminals 46 (see FIG. 1) of the exposed portion 402 and the second terminals 56 (see FIG. 1) of the exposed portion 502. For example, the first terminals 46 and the second terminals 56 can be used to measure the contact resistance between the first contact point 48 and the second contact point 58 by using the four-terminal method.

The first conductive pattern 44 and the second conductive pattern 54 illustrated in FIGS. 5 and 7 are abstract conductive patterns for simple explanation about the present invention and have no specific function. In other words, even when the illustrated first contact point 48 and the illustrated second contact point 58 are brought into contact with each other, the device 10 does not work as an electronic device.

For example, the actual first conductive pattern 44 and the actual second conductive pattern 54 are formed with an electronic circuit (not shown) which can measure the electric pulse of the heart of the subject. Referring to FIG. 3, the first conductive pattern 44 of the exposed portion 402 may be formed with a conductive portion (not shown), which can be brought into contact with a skin of the subject, instead of the first terminals 46. The second conductive pattern 54 of the exposed portion 502 may be formed with a display with light emitting diode (LED) instead of the second terminals 56. In this instance, the electronic circuit can obtain biological signals generated from electric pulse of the heart of the subject and can show the measurement result on the display.

The exposed portion 402 (exposed portion 502) may be provided not only the conductive portion (electrode) and the display described above but also components in accordance with use of the device 10. For example, the exposed portion 402 (exposed portion 502) may be provided with a sensing surface of a sensor such as a humidity sensor and a gas sensor, a light-receiving portion of a photodetector and a light-emitting portion of a light-emitting element.

Referring to FIG. 5, each of the number of the first contact point 48 and the number of the second contact point 58 of the present embodiment is one. However, the present invention is not limited thereto. For example, each of the number of the first contact points 48 and the number of the second contact points 58 may be two or more.

Referring to FIGS. 1 and 2, each of the number of the exposed portion 402 and the number of the exposed portion 502 of the present embodiment is one. However, the present invention is not limited thereto. For example, each of the number of the exposed portions 402 and the number of the exposed portions 502 may be two or more. Moreover, the device 10 may have only the one exposed portion 402 or may have only the one exposed portion 502. Thus, at least one of the first circuit member 40 and the second circuit member 50 should comprise the exposed portion 402 (exposed portion 502) and the seal portion 404 (seal portion 504). Referring to FIG. 6, the first contact point 48 should be in contact with the second contact point 58 in the fabricated device. Each of the exposed portion 402 and the exposed portion 502 should be exposed outward of the fabricated device 10.

Hereafter, more specific explanation will be made about the device 10 of the present embodiment.

Referring to FIGS. 1 and 2, the first film 22 of the present embodiment has a first inner portion 222 and a first outer portion 224. The first outer portion 224 of the present embodiment has a first seal portion 226 and a first contact portion 228. The first inner portion 222 is located inward of the first outer portion 224 in the XY-plane. In other words, the first outer portion 224 is a part of the first film 22 which surrounds the first inner portion 222.

Referring to FIG. 2, the second film 32 of the present embodiment has a second inner portion 322 and a second outer portion 324. The second outer portion 324 of the present embodiment has a second seal portion 326 and a second contact portion 328. The second inner portion 322 is located inward of the second outer portion 324 in the XY-plane. In other words, the second outer portion 324 is a part of the second film 32 which surrounds the second inner portion 322.

Referring to FIGS. 1 and 2, the first inner portion 222 of the first film 22 and the second inner portion 322 of the second film 32 of the device 10 are parts for accommodating the circuit structure 12 and are apart from each other. The first seal portion 226 and the second seal portion 326 of the present embodiment are bonded together to form a seal trace 16. According to the present embodiment, the first seal portion 226 and the second seal portion 326 are bonded together by heat-sealing. Thus, the seal trace 16 of the present embodiment is a trace where the first seal portion 226 and the second seal portion 326 are welded to each other by heat-treatment. However, the present invention is not limited thereto, but the first seal portion 226 and the second seal portion 326 can be bonded together by various methods such as high frequency, ultrasonic, laser or adhesive.

The seal trace 16 of the present embodiment is formed throughout entire circumference of the first seal portion 226 and the second seal portion 326. The seal trace 16 surrounds the first contact portion 228 and the second contact portion 328 throughout their entire circumference in the XY-plane. However, the present invention is not limited thereto, but the seal trace 16 may be formed on a necessary part in accordance with the forming method of the device 10. For example, the seal trace 16 may be partially formed or may not be formed at all.

Referring to FIG. 6, as described later, the inside of the device 10 is vacuumed after the first seal portion 226 and the second seal portion 326 are bonded together. According to the present embodiment, upon vacuuming, the first contact portion 228 and the second contact portion 328 are brought into contact with each other in a contact region 17 because of air pressure difference. As a result, the device 10 is formed with a closed space 18. The closed space 18 is enclosed by the first inner portion 222 and the second inner portion 322. The contact region 17 of the present embodiment seamlessly surrounds the first inner portion 222 and the second inner portion 322 throughout their entire circumference in the XY-plane. However, the present invention is not limited thereto, but the contact region 17 may be formed on a necessary part in accordance with the forming method of the device 10. For example, the contact region 17 may be partially formed or may not be formed at all.

The closed space 18, which is formed as described above, is enclosed by the first sealing member 20 and the second sealing member 30 except for the exposed portion 402 and the exposed portion 502 and is shut off from an outer space outside the device 10. According to the present embodiment, the first seal portion 226 and the second seal portion 326 are firmly bonded together. In addition, the contact region 17 is located inward of the seal trace 16 in the XY-plane and blocks air which might flow between the inside and the outside of the closed space 18. Thus, air pressure in the closed space 18 is kept to low pressure lower than the atmospheric pressure.

The first circuit member 40 and the second circuit member 50 except the exposed portion 402 and the exposed portion 502 are shut in the closed space 18 which is kept to the aforementioned low pressure. In other words, except for the exposed portion 402 and the exposed portion 502, no part of the first circuit member 40 and the second circuit member 50 is located outside the device 10. The first contact point 48 and the second contact point 58 are pressed against each other to be in contact with each other in the closed space 18. In detail, a contact force is generated between the first contact point 48 and the second contact point 58 because of air pressure difference between the inside and the outside of the closed space 18. The first contact point 48 and the second contact point 58 are pressed against each other because of this air pressure difference. Therefore, the contact between the first contact point 48 and the second contact point 58 can be securely kept.

Summarizing the explanation described above, the first sealing member 20 and the second sealing member 30 of the device 10 of the present embodiment overlap with each other to be in contact with each other while the first circuit member 40 and the second circuit member 50 (hereafter, simply referred to as "circuit members") are sandwiched therebetween. Each of the first sealing member 20 and the second sealing member 30 of the present embodiment is basically formed of a film.

Moreover, the structure of each of the circuit members is not restricted except that each of the circuit members should be provided with the contact point which is the first contact point 48 or the second contact point 58. Thus, each of the circuit members of the present embodiment has a simple structure and can be formed of various material. For example, each of the circuit members may be an insulation film formed with the conductive pattern, i.e., the first conductive pattern 44 or the second conductive pattern 54, having the contact point. In this instance, the thickness of the entire device 10 can be made extremely thin. Thus, the present embodiment provides the device 10 which is new and can be made thinner.

According to the present embodiment, the first seal portion 226 and the second seal portion 326 are bonded together, and the first contact portion 228 and the second contact portion 328 are in contact with each other. According to this structure, the closed space 18 can be reliably kept airtight. However, the present invention is not limited to the present embodiment. For example, the first seal portion 226 and the second seal portion 326 may partially surround the first contact portion 228 and the second contact portion 328 in the XY-plane. The first seal portion 226 and the second seal portion 326 may partially surround the first inner portion 222 and the second inner portion 322 in the XY-plane.

According to the present embodiment, the first circuit member 40 and the second circuit member 50 can be easily taken out from the closed space 18 by cutting off the first seal portion 226 and the second seal portion 326. Thereafter, each of the first circuit member 40 and the second circuit member 50 can be easily separated from the first seal portion 226 and the second seal portion 326 by peeling off the frame films 26. Thus, according to the present embodiment, the members can be easily collected separately.

According to the present embodiment, the outer surface 232 of the first film 22 is located outside the closed space 18. The film-seal portions 262 of the frame films 26 are bonded on the thus-arranged outer surface 232. The exposed portion 402 and the exposed portion 502 are exposed to the outer space located outside the device 10. If none of the exposed portion 402 and the exposed portion 502 as described above is provided, electronic circuits (not shown) formed in the first conductive pattern 44 and the second conductive pattern 54 should obtain biological signals of a subject with no contact with the subject. For example, the electronic circuits should obtain biological signals of the subject by contactless communication. However, weak biological signals are difficult to be accurately obtained by contactless communication. In contrast, according to the present embodiment, biological signals can be accurately obtained via a conductive portion (not shown) which is provided on the exposed portion 402 or the exposed portion 502 and is in contact with a skin of the subject.

Each of the first sealing member 20 and the second sealing member 30 is preferred to have a high barrier property against oxygen. More specifically, each of the first film 22 and the second film 32 (or rigid circuit board) is preferred to comprise a layer made of high oxygen barrier material which is material having a high barrier property against oxygen. According to this layer-structure, oxidation of the metal members of the circuit structure 12 can be reduced.

For example, the high oxygen barrier material may be linear low-density polyethylene (LLDPE). More specifically, the high oxygen barrier material may be PET/Al/PE which is formed by laminating polyethylene terephthalate, aluminum and polyethylene; ON/PE which is formed by laminating biaxially stretched nylon and polyethylene; PET/EVOH/PE which is formed by laminating polyethylene terephthalate, polyvinyl chloride and polyethylene; or may be formed by laminating a transparent high barrier film and polyethylene. The transparent high barrier film may be polyethylene terephthalate (PET) deposited with SiOx or aluminum oxide.

Each of the first sealing member 20 and the second sealing member 30 of the present embodiment is preferred to have a high barrier property against water vapor in addition to the high barrier property against oxygen. More specifically, each of the first film 22 and the second film 32 (or rigid circuit board) is preferred to comprise a layer made of high water-vapor barrier material which is material having a high barrier property against water vapor. According to this layer-structure, the circuit structure 12 can be water-proofed. For example, the high water-vapor barrier material may be material which is a sheet made of ON/PE, biaxially stretched polypropylene (OPP) or PET and is coated with polyvinylidene chloride (PVDC).

Each of the first sealing member 20 and the second sealing member 30 may have various barrier properties such as a barrier property against nitrogen in addition to the high barrier property against oxygen and the high barrier property against water vapor. Thus, each of the first sealing member 20 and the second sealing member 30 is preferred to have high barrier properties in accordance with its use.

The device 10 (see FIG. 1) of the present embodiment is formed via four steps consisting of a preparing step (STEP 1), a stacking step (STEP 2), a shutting-in step (STEP 3) and a vacuuming step (STEP 4). However, the present invention is not limited thereto, but the forming method of the device 10 can be modified as necessary. Hereafter, explanation will be made about an example of the forming method of the device 10 of the present embodiment.

Referring to FIG. 9, first, in the preparing step, the first sealing member 20, the second sealing member 30, the first circuit member 40 and the second circuit member 50 are prepared.

Then, in the stacking step, the first sealing member 20, the first circuit member 40, the second circuit member 50 and the second sealing member 30 are stacked on each other in this order from top to bottom along the Z-direction. Meanwhile, the first circuit member 40 and the second circuit member 50 are arranged so that the first contact point 48 and the second contact point 58 face each other in the Z-direction. Moreover, the exposed portion 402 and the exposed portion 502 are arranged so as to face the center holes 266 (see FIG. 7) of the frame films 26 in the Z-direction, respectively. The additional film 38 is located at the middle of second film 32 in the XY-plane. The first circuit member 40 and the second circuit member 50 are located at the middle of the additional film 38 in the XY-plane. In addition, the first film 22 and the second film 32 are arranged so that two of the meltable layers 146 (see FIG. 7) thereof face each other in the Z-direction.

Figure 10:
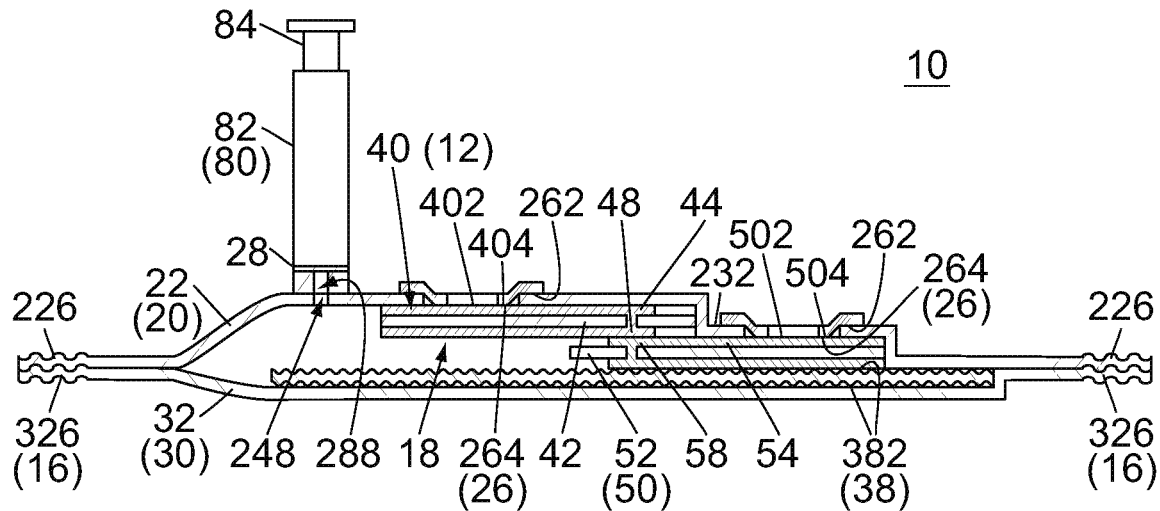
FIG. 10 is a schematic, cross-sectional view showing the device of FIG. 1, taken along line VI-VI, wherein the device is under manufacturing process, the inner structure of the device is merely schematically illustrated, the size and arrangement of each member are not equal to the actual size and arrangement thereof, and a side surface of an instrument for vacuuming is illustrated.

Referring to FIG. 10, then, in the shutting-in step, the circuit-seal portions 264 of the frame films 26 are pressed against and adhered to the exposed portion 402 and the exposed portion 502, respectively. Then, ultraviolet light is radiated to the frame films 26 so that the film-seal portions 262 are bonded to the first film 22 and that the circuit-seal portions 264 are bonded to the exposed portion 402 and the exposed portion 502. Then, heat-sealing is applied to the first film 22 and the second film 32. In detail, parts of the two meltable layers 146 (see FIG. 7), which are located at outer circumferences of the first film 22 and the second film 32 in the XY-plane, are welded to each other via heat-sealing. As a result of the heat-sealing, the device 10 with the seal trace 16 is formed. The device 10 has an inner space which is enclosed by the first sealing member 20 and the second sealing member 30 and which is shut off from the outside of the device 10 except for the air valve 28.

Then, in the vacuuming step, the inside of the device 10 is vacuumed. According to the present embodiment, the air valve 28 and an instrument 80 are used to discharge the air of the inside of the device 10. The instrument 80 of the present embodiment is a syringe-type piston pump. The instrument 80 comprises a syringe 82 and a plunger 84. The syringe 82 has a lower end which has a ring shape in the XY-plane. The ring shape of the syringe 82 corresponds to the outer circumference of the cover portion 282 of the air valve 28.

In the vacuuming step, first, the lower end of the syringe 82 is pressed against the upper surface of the cover portion 282 (see FIG. 8). Then, the plunger 84 is pulled upward. Meanwhile, the air valve 28 takes the open state, and an air passage is formed between the inside of the device 10 and the inside of the syringe 82. The air in the inside of the device 10 is discharged into the inside of the syringe 82 through the passing hole 288 and the cuts 285 (see FIG. 8) of the air valve 28. As a result, air pressure of the inside of the device 10 is gradually lowered. When air pressure of the inside of the device 10 becomes low pressure close to that of a vacuum, the vacuuming by using the instrument 80 is stopped.

Referring to FIG. 6 together with FIG. 10, when the vacuuming is stopped, the valves 284 (see FIG. 8) of the air valve 28 cover the cuts 285 (see FIG. 8) because of air pressure difference between air pressure of the inside of the device 10 and the atmospheric pressure, and thereby the air valve 28 takes the closed state. As a result, air pressure of the inside of the device 10 is kept to low pressure. Thus, the device 10 is formed with the closed space 18 which is shut off from the outside and has the low pressure. The first contact point 48 and the second contact point 58 are pressed against each other and are brought into contact with each other because of air pressure difference between the inside and the outside of the closed space 18.

The first film 22 and the second film 32 tend to be in close contact with each other upon vacuuming, and thereby tend to form a close contact part such as the contact region 17. If the additional film 38 is not provided, the close contact part of the first film 22 and the second film 32 will be formed in the closed space 18. The thus-formed close contact part might block an air passage between the air valve 28 and a contact point region where the first contact point 48 and the second contact point 58 are arranged. As a result, air pressure of a space in which the first contact point 48 and the second contact point 58 are located might be insufficiently lowered, and thereby the first contact point 48 and the second contact point 58 might be unreliably brought into contact with each other.

In contrast, since the additional film 38 of the present embodiment is located between the first film 22 and the second film 32, direct contact between the first film 22 and the second film 32 is prevented. Moreover, since the additional film 38 has the uneven portion 382, the air passage through the air valve 28 can be kept even in a case where the first film 22 and the second film 32 are indirectly brought into contact with each other via the additional film 38. Therefore, the first contact point 48 and the second contact point 58 can be reliably brought into contact with each other.

The additional film 38 of the present embodiment is an embossed film distinct and separable from the second film 32 and is arranged on the second film 32. The uneven portion 382 is formed over upper and lower surfaces of the additional film 38. However, the present invention is not limited thereto. For example, the additional film 38 may be adhered to and fixed on an upper surface of the second film 32. The uneven portion 382 may be formed only on the upper surface of the additional film 38. The second film 32 may be embossed so as to be formed with the uneven portion 382. In this instance, the additional film 38 does not need to be provided. Thus, the second sealing member 30 may comprise only the second film 32 which has the uneven portion 382.

The additional film 38 of the present embodiment forms the second sealing member 30 together with the second film 32. However, the present invention is not limited thereto. For example, the additional film 38 may form the first sealing member 20 together with the first film 22. More specifically, the additional film 38 may be arranged under the first film 22. Moreover, the first film 22 may be embossed so as to be formed with the uneven portion 382. In this instance, the additional film 38 does not need to be provided.

According to the forming method of the present embodiment, the first contact point 48 and the second contact point 58 are securely in contact with each other without using a fixing member such as an adhesive. Therefore, when the device 10 is no longer used, the device 10 can be disassembled merely by peeling off the frame films 26 after cutting off the first outer portion 224 and the second outer portion 324. In addition, the first circuit member 40 and the second circuit member 50 can be shut in the closed space 18 having low pressure, and thereby degradation of the metal members due to oxidation can be reduced, for example.

Referring to FIG. 10, according to the forming method of the present embodiment, the simple instrument 80 can be used for easy vacuuming. The vacuuming by the instrument 80 can be repeatedly performed. For example, even when air pressure in the closed space 18 becomes higher during use of the device 10, the instrument 80 can be used for vacuuming again. Thus, during use of the device 10, the contact force between the first contact point 48 and the second contact point 58 can be kept. However, the present invention is not limited thereto, but the forming method of the device 10 can be modified as necessary.

For example, the structure of the instrument 80 is not specifically limited, provided that it can be used for vacuuming. A nozzle may be used instead of the illustrated instrument 80. The nozzle may be inserted into and vacuum the device 10. In this instance, the air valve 28 does not need to be provided. Alternatively, a commercially available desktop vacuum packaging machine (not shown) may be used for sealing and vacuuming. Referring to FIG. 9, the members of the device 10 may be arranged in a chamber (not shown) so that vacuuming is performed simultaneously with heat-sealing. According to this forming method, the additional film 38 does not need to be provided. In addition, the other member does not need to be provided with the uneven portion 382. However, a commercially available, simple instrument such as the instrument 80 (see FIG. 10) is preferable from a viewpoint of easy fabrication of the device 10.

According to the forming method of the present embodiment, the frame films 26 have been adhered to the first film 22 when the preparing step starts. The frame films 26 are bonded to the first film 22, the first circuit member 40 and the second circuit member 50 in the sealing step. However, the present invention is not limited thereto. For example, the frame films 26 may be adhered to the first film 22 in the sealing step. The frame films 26 may be bonded to the first film 22, the first circuit member 40 and the second circuit member 50 by radiating ultraviolet light after the vacuuming step ends. However, the forming method of the present embodiment is preferable from a viewpoint of reliably vacuuming the inside of the device 10.

The present embodiment can be further variously modified as described below in addition to the already described modifications.

Figure 11:
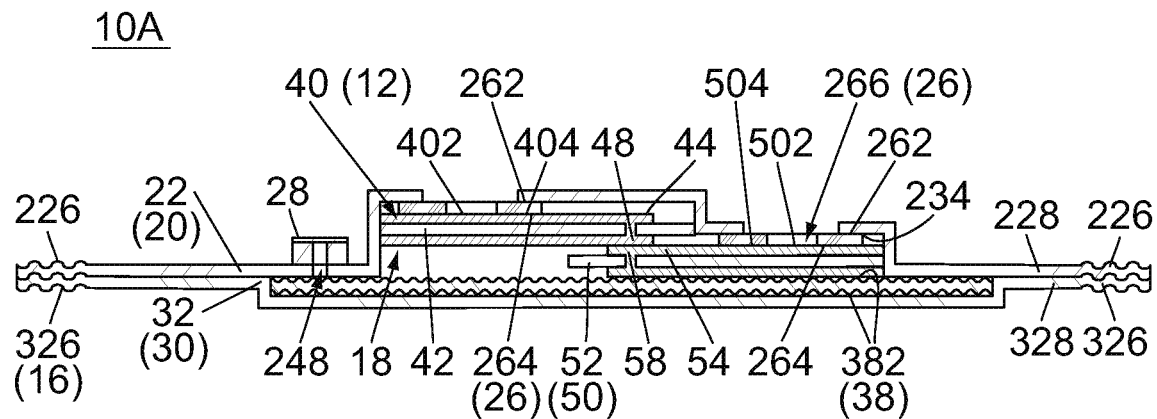
FIG. 11 is a cross-sectional view showing a modification of the device of FIG. 6, wherein an inner structure of the device is merely schematically illustrated, and the size and arrangement of each member are not equal to the actual size and arrangement thereof.
Figure 12:
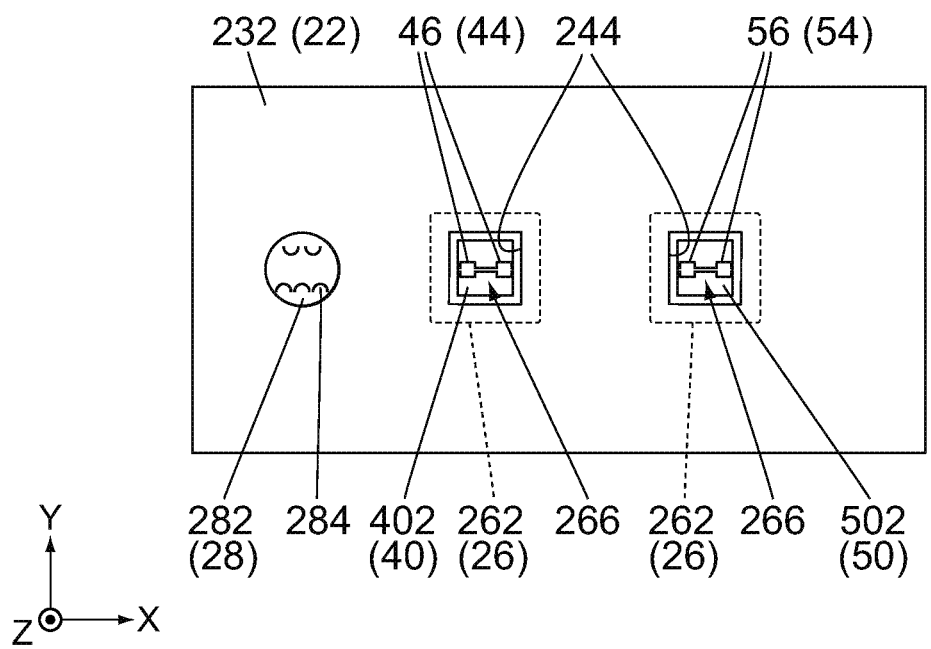
FIG. 12 is a top view showing the device of FIG. 11, wherein hidden outlines of the frame films are illustrated with dashed line.
Figure 13:
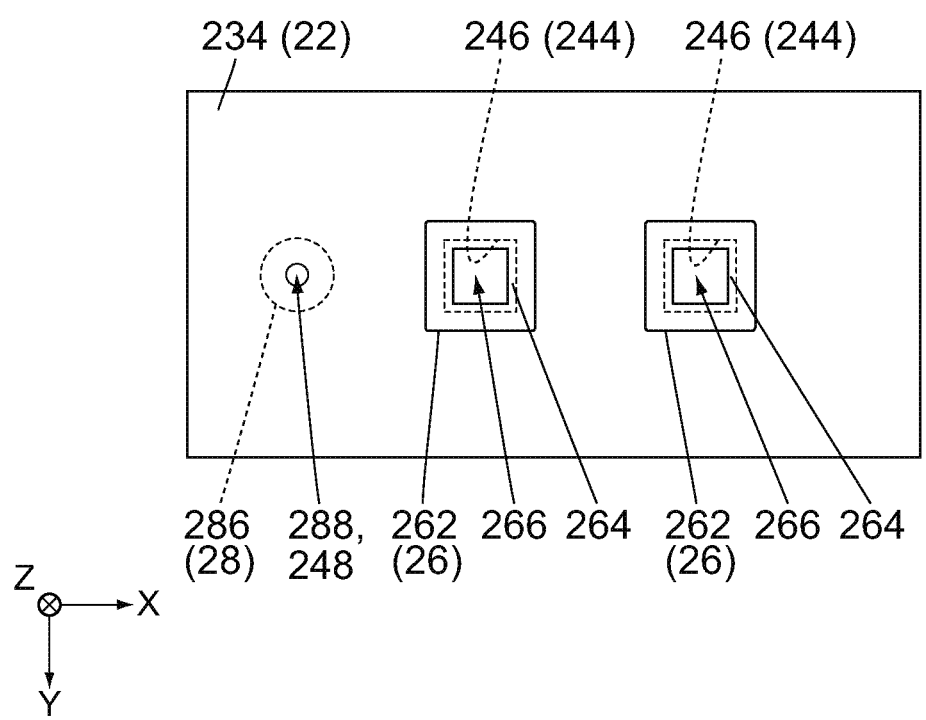
FIG. 13 is a bottom view showing the first sealing member of the device of FIG. 12, wherein hidden outlines of the frame films and the air valve are illustrated with dashed line.
Figure 14:
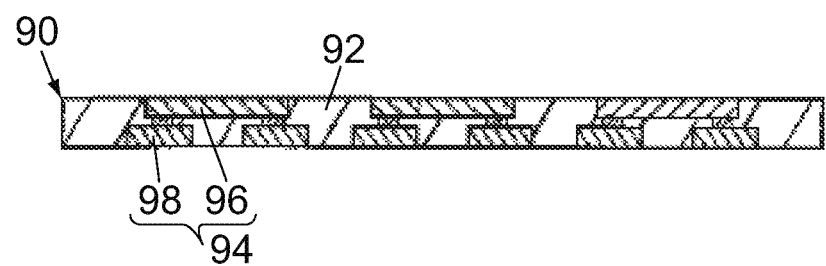
FIG. 14 is a cross-sectional view showing a device of Patent Document 1.

Comparing FIG. 11 with FIG. 6, a device 10A according to a first modification comprises the first sealing member 20, the second sealing member 30, the first circuit member 40 and the second circuit member 50 same as those of the device 10. However, the frame films 26 of the first sealing member 20 are arranged inside the device 10A. For each of the frame films 26, each of the upper layer and the lower layer contains a pressure-sensitive adhesive and an ultraviolet-curing resin. Referring to FIG. 11, the inner surface 234 of the first film 22 of the device 10A is located inside the closed space 18. Referring to FIGS. 11 to 13, the film-seal portions 262 of the frame films 26 of the device 10A are bonded on the thus-arranged inner surface 234.

Except for the differences described above, the device 10A has a structure similar to that of the device 10 and works similarly to the device 10. Thus, according to the present modification, the effect similar to that of the aforementioned embodiment can be obtained.

Each of the frame films 26 of the present modification has the structure same as that of the frame films 26 of the aforementioned embodiment except that the upper layer thereof contains the pressure-sensitive adhesive and the ultraviolet-curing resin. However, the present invention is not limited thereto but can be further modified. For example, the upper layer of the frame film 26 may be a meltable layer (not shown). The lower layer of the frame film 26 may be an ultraviolet-curing tape. In this instance, the upper layer of the frame film 26 may work as the film-seal portion 262, and the lower layer of the frame film 26 may work as the circuit-seal portion 264.

According to the aforementioned modification, each of the film-seal portions 262, which is the meltable layer, and the meltable layer 146 (see FIG. 7) of the first film 22 can be fused to each other, and thereby the frame films 26 can be bonded to the inner surface 234 of the first film 22. Moreover, the frame films 26 can be bonded to the seal portion 404 and the seal portion 504 by radiating ultraviolet light after the circuit-seal portions 264 are pressed against the seal portion 404 and the seal portion 504.

Referring to FIGS. 12 and 13, according to the aforementioned modification, the size of each of the openings 244 in the XY-plane may be smaller than the size of the center hole 266 of the corresponding frame film 26 in the XY-plane. Each of the frame films 26 may be arranged on the inner surface 234 of the first film 22 so that the corresponding opening 244 is located inward of the center hole 266 in the XY-plane.

Referring to FIG. 7, the peripheral edge 229 of the first film 22 and the peripheral edge 329 of the second film 32 may be connected to each other at a rear end (negative X-side end) thereof in a front-rear direction (X-direction). In other words, each of the first film 22 and the second film 32 may be a part of a single planar sheet which is folded so that the first film 22 and the second film 32 overlap with each other. Instead, the peripheral edge 229 of the first film 22 and the peripheral edge 329 of the second film 32 may be connected to each other except for the rear end thereof. In other words, each of the first film 22 and the second film 32 may be a part of a single folder-like sheet.

The aforementioned folder-like sheet may have an openable and closable fastener which is provided on a rear end part thereof. In this instance, vacuuming may be performed under a state where the fastener is closed. Thereafter, parts of the first film 22 and the second film 32 which are located forward (positive X-side) of the fastener may be fused to each other. The part provided with the air valve 28 may be cut off after the fusing.

The first circuit member 40 may be a member integral to the first sealing member 20. The second circuit member 50 may be a member integral to the second sealing member 30. For example, the first base portion 42 may be adhered to and fixed on a lower surface of the first film 22. Instead, the first conductive pattern 44 may be formed on the lower surface of the first film 22. The second circuit member 50 may be provided on the additional film 38. For example, the second base portion 52 may be adhered to and fixed on the upper surface of the additional film 38. Instead, the second conductive pattern 54 may be formed on the upper surface of the additional film 38. Moreover, when the second sealing member 30 does not comprise the additional film 38, the second base portion 52 may be adhered to and fixed on the upper surface of the second film 32. Instead, the second conductive pattern 54 may be formed on the upper surface of the second film 32.

Instead of the additional film 38, the device 10 (device 10A) may comprise a cushioning material (not shown) formed of an open-cell structure such as a urethane sponge. The cushioning material may be arranged above the first circuit member 40 or may be arranged under the second circuit member 50. In any instance, the cushioning material should be located at a position which corresponds to the first contact point 48 and the second contact point 58 in the XY-plane.

When the cushioning material as described above is provided, the cushioning material is compressed upon vacuuming. The first contact point 48 and the second contact point 58 are pressed against each other by the restoring force of the compressed cushioning material. Moreover, even if air flows into the closed space 18, the air is absorbed into the cushioning material. In this situation, since the restoring force of the cushioning material is only slightly reduced, the change in the contact force between the first contact point 48 and the second contact point 58 can be reduced. The present modification provides the device 10 (device 10A) which can stably work for a long time under various environments.

What is claimed is:

1. A device comprising a first sealing member, a second sealing member, a first circuit member and a second circuit member, wherein:
   the first sealing member comprises, as a base of the first sealing member, a first film and a frame film;
   the first film is formed with an opening;
   the opening is surrounded by an edge portion which forms a closed path;
   the frame film has a closed path shape;
   at least one of the first circuit member and the second circuit member comprises an exposed portion and a seal portion;
   the exposed portion and the seal portion face the first film;
   the seal portion surrounds the exposed portion throughout its entire circumference;
   the frame film has a film-seal portion and a circuit-seal portion;
   the film-seal portion is bonded to the first film so as to surround the opening throughout its entire circumference;

the circuit-seal portion is bonded to the seal portion so as to surround the exposes portion throughout its entire circumference;
the device is formed with a closed space;
the closed space is enclosed by the first sealing member and the second sealing member except for the exposed portion and is shut off from an outer space located outside the device;
the exposed portion is exposed to the outer space located outside the device;
the first circuit member and the second circuit member except the exposed portion are shut in the closed space;
the first circuit member comprises a first contact point;
the second circuit member comprises a second contact point; and
the first contact point and the second contact point are pressed against each other to be in contact with each other in the closed space.

2. The device as recited in claim 1, wherein:
the first film has an outer surface;
the outer surface is located outside the closed space; and
the film-seal portion of the frame film is bonded on the outer surface.

3. The device as recited in claim 1, wherein:
the first film has an inner surface;
the inner surface is located inside the closed space; and
the film-seal portion of the frame film is bonded on the inner surface.

4. The device as recited in claim 1, wherein the frame film is formed of an ultraviolet-curing tape.

5. The device as recited in claim 1, wherein the second sealing member comprises, as a base of the second sealing member, a second film.

\* \* \* \* \*